United States Patent [19]
DeMarco et al.

[11] Patent Number: 5,817,064
[45] Date of Patent: Oct. 6, 1998

[54] SYRINGE NEEDLE GUARD

[75] Inventors: Anthony O. DeMarco, Blue Bell; Stephen W. Goodsir, Wayne, both of Pa.

[73] Assignee: American Home Products Corporation, Madison, N.J.

[21] Appl. No.: 720,982

[22] Filed: Oct. 15, 1996

Related U.S. Application Data

[60] Provisional application No. 60/005,815 Oct. 23, 1995.

[51] Int. Cl.⁶ .................................................. A61M 5/00
[52] U.S. Cl. .......................... 604/198; 604/263; 604/232
[58] Field of Search .................................... 604/198, 192, 604/187, 263, 110, 232

[56] References Cited

U.S. PATENT DOCUMENTS

| | | |
|---|---|---|
| 4,631,057 | 12/1986 | Mitchell . |
| 4,681,567 | 7/1987 | Masters et al. . |
| 4,772,272 | 9/1988 | McFarland . |
| 4,840,619 | 6/1989 | Hughes ................................ 604/192 X |
| 4,842,587 | 6/1989 | Poncy . |
| 4,961,730 | 10/1990 | Poncy ................................... 604/263 X |
| 4,976,702 | 12/1990 | Andrews et al. . |
| 4,998,924 | 3/1991 | Ranford . |
| 5,019,051 | 5/1991 | Hake . |
| 5,045,066 | 9/1991 | Scheuble et al. ........................ 604/198 |
| 5,084,030 | 1/1992 | Byrne et al. . |
| 5,254,100 | 10/1993 | Huband ................................... 604/198 |
| 5,279,579 | 1/1994 | D'Amico ................................ 604/192 |

*Primary Examiner*—John D. Yasko
*Attorney, Agent, or Firm*—Arnold S. Milowsky

[57] ABSTRACT

A cartridge syringe with a slideable protective sheath to prevent accidental needle sticks following administration of a an injection is described. The device comprises a syringe cartridge, comprising a constricted distal end region, a piston movably disposed within the barrel, a hub having an axial bore mounted to the constricted distal end region of the barrel, and a hollow needle, the proximal end of the hollow needle projecting through the axial bore of the hub and the distal end of the needle having a pointed tip; and a protective sheath having an inner diameter greater than the external diameter of the syringe cartridge, such that the protective sheath is slideably movable substantially coaxially along the external surface of the cartridge barrel from a first position in which the tip of the needle extends past both ends of the protective sheath, to a second position in which the distal end of the sheath extends past the tip of the needle.

7 Claims, 3 Drawing Sheets

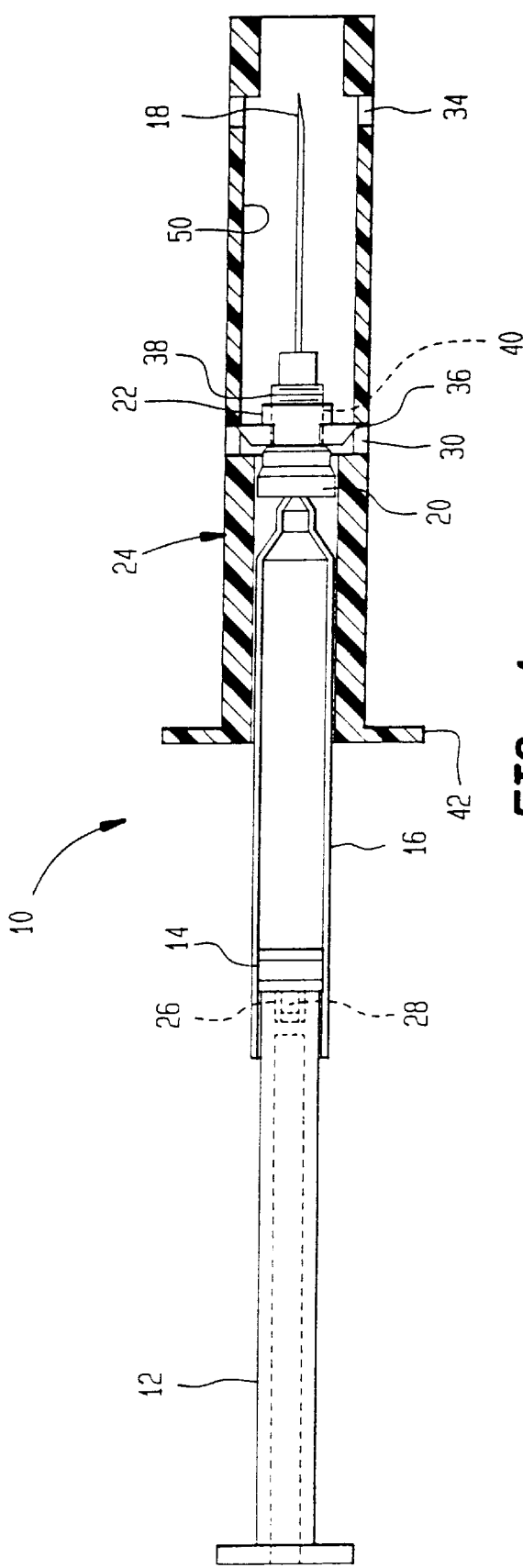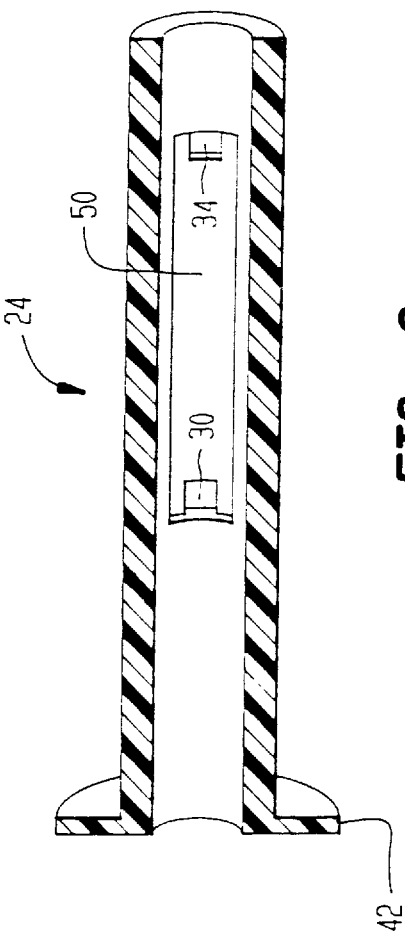

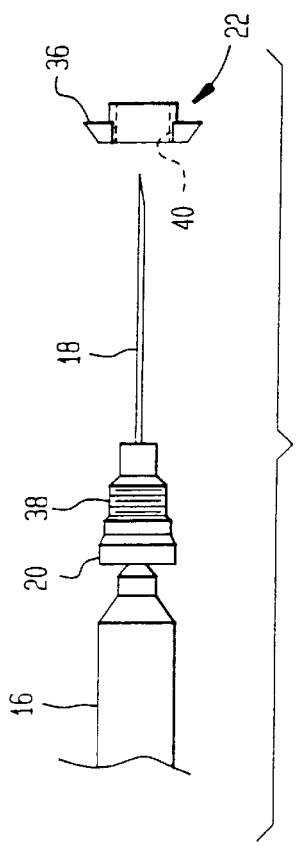
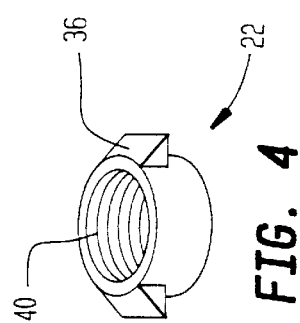
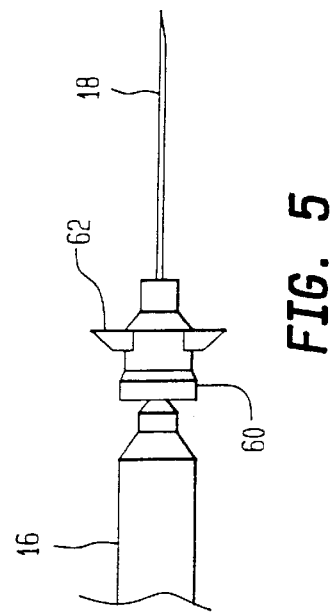
FIG. 3
FIG. 4
FIG. 5

SYRINGE NEEDLE GUARD

BACKGROUND OF THE INVENTION

This application claims the benefit of U.S. provisional application Ser. No. 60/005,815, filed Oct. 23, 1995.

This invention relates to improvements in syringes in general, and more specifically prefilled ones, by providing a safety shield mounted on a syringe to prevent accidental needle sticks following administration of a substance contained in the syringe.

Prefilled syringe cartridges have become a convenient method of administering premeasured quantities of pharmacologic agents. The use of prefilled syringe cartridges provides several advantages over conventional syringes by alleviating the need for measuring individual doses from larger storage containers. The premeasured dosages prevent the possibility of contamination of the larger container, provides an added measure of sterility for the dose to be administered, and reduces the possibility of product tampering. One such example of a prefilled syringe cartridge system is the TUBEX closed injection system which is manufactured by Wyeth-Ayerst Laboratories. The TUBEX closed injection system provides sterile premeasured doses of antibiotics, barbiturates, biological vaccines, cardiovascular agents, heparin lock flush kits, narcotic agents, vitamins, and several other specialized agents.

Accompanying the use of conventional syringes or prefilled syringe cartridges for parenteral administration of drugs, is the risk of accidental needle sticks by health care workers. The problem of accidental needle sticks by medical personnel while working with syringes has become acute with the increase in the seriousness of diseases such as AIDS, hepatitis, infectious mononucleosis, Burkitt's lymphoma, adult T-cell leukemia, and venereal diseases that are can be caused by blood transmissible viruses. For conventional syringes, numerous devices have been developed to either shield the needle after use or cause the needle to retract after use.

The use of prefilled syringe cartridges, offers some protection over conventional syringes against accidental needle sticks by providing a narrow cartridge for easy disposal in a puncture proof container and by virtue of the cartridge design the hands of the health care worker are placed further from the needle than with a conventional syringe. While the use of prefilled syringe cartridges provides a decreased risk of accidental needle sticks over conventional syringes, no satisfactory protective shield has been developed for prefilled cartridge syringes which would significantly minimize or prevent the possibility of accidental needle sticks, without radically modifying the prefilled syringe cartridge.

SUMMARY OF THE INVENTION

This invention provides a cartridge syringe with a slideable protective sheath to cover the needle tip of a cartridge syringe to prevent accidental needle sticks following the administration of a pharmacologic agent. The cartridge may be prefilled with a substance to be administered, or unfilled to allow for filling with an injectable material immediately before use.

More specifically, this invention preferrably provides a prefilled cartridge syringe with a slideable protective sheath which comprises a prefilled syringe cartridge having a cartridge barrel with an internal and external surface, the cartridge barrel having a constricted distal end region, a piston movably disposed within the barrel, a hub having an axial bore mounted to the constricted distal end region of the barrel, and a hollow needle, the proximal end of the hollow needle projecting through the axial bore of the hub and the distal end having a pointed tip; a plunger releasably affixed to the piston; a protective sheath having an inner diameter greater than the external diameter of the prefilled syringe cartridge, and a plurality of interlocking means; and mounting means for mounting the protective sheath to the hub, the mounting means containing unidirectional locking means such that the protective sheath is slideably movable substantially coaxially along the external surface of the cartridge barrel from a first position in which the first interlocking means and unidirectional locking means are releasably engaged so that the tip of the needle extends past both ends of the protective sheath, to a second position in which the unidirectional locking means and second interlocking means are engaged so that the distal end of the sheath extends past the tip of the needle and the protective sheath cannot be retracted to a position in which the needle is exposed past the distal end of the protective sheath.

In a first embodiment, the prefilled syringe cartridge is a TUBEX closed injection system which requires no modification to be used with the protective sheath. In this embodiment, the hub of the TUBEX closed injection system contains external threads which receive the mounting means. In this first embodiment, the mounting means contain unidirectional locking means which are unidirectional releasably engaged with the first interlocking means of the sheath in a first position in which the needle is exposed past the distal end of the sheath. Following the administration of an injection, pressure is applied to the sheath to disengage the unidirectional locking means from the first interlocking means and the sheath is pushed toward the distal end of the needle to a second position in which the unidirectional locking means are engaged with the second interlocking means. In this second position, the sheath is extended distally past the end of the needle by an amount sufficient to prevent accidental contact with the needle tip. In the first embodiment, the unidirectional locking means are shaped so that the sheath can only be moved from the first position toward the distal end of the of the needle.

In the first embodiment it is preferred that there are two longitudinal channels on a portion of opposing sides of the inside of the sheath. In this embodiment, the mounting means comprises an internally threaded collar. The unidirectional locking means comprise two ears on opposing sides of the collar, in which the proximal side of each of the ears is angled to allow the sheath to slide forward and the distal side each of the ears is flat and perpendicular relative to the longitudinal axis of the sheath, thereby providing unidirectional motion of the sheath after the unidirectional locking means are disengaged from the first interlocking means. The two ears are positioned in the longitudinal channels of the sheath to allow movement between the first and second positions. In this embodiment, the interlocking means comprise first and second pockets in the longitudinal channels of the sheath and define where the first and second positions are. The longitudinal channels extend from the first interlocking means to the second interlocking means of the sheath, thereby preventing motion of the sheath distally beyond the second position.

In a second embodiment, the hub and mounting means with ears comprise one unitary piece.

In a third embodiment, the device described in the preferred first embodiment is provided as a preassembled tamper evident syringe assembly in which the unidirectional locking means are positioned in the first pocket. In this embodiment, a tamper evident needle cover/plunger containing means for attaching to the piston is breakably attached to the distal end of the sheath, and a tamper evident sheath cover is breakably attached to the proximal end of the sheath cover. Both the sheath cover and needle cover/plunger are breakably attached via a snap ring. With the inner surface of the needle cover/plunger being in contacting the hub via a snug friction fit, the TUBEX closed injection system is provided with an added measure of sterility. The presence of the sheath cover and needle cover/plunger and intact snap rings immediately prior to use also provide an indication that the device was not tampered with following assembly. Immediately prior to use, the sheath cover and needle cover/plunger are removed from the sheath by applying force along the respective snap rings, such as by bending or twisting slightly. The sheath cover can be discarded, and the needle cover/plunger attached to the piston via the attachment means on the needle cover/plunger, where it can be used as a plunger for giving an injection as described above.

This invention therefore provides substantial advantages over the presently existing syringe protection devices by providing a safety sheath to prevent needle sticks for a TUBEX closed injection system either without modifying the existing TUBEX closed injection system at all, or only requiring minor external modifications to the existing TUBEX closed injection system, and additional features to aid in preventing contamination of the needle and indicating whether tampering has occurred.

BRIEF DESCRIPTION OF THE DRAWINGS

FIG. 1 is a sectional view of the first preferred embodiment showing the TUBEX closed injection system and protective sheath, with the protective sheath locked in the second position.

FIG. 2 is a cross-sectional view of the protective sheath which shows the sheath, a longitudinal channel, and first and second pockets.

FIG. 3 is an exploded partial side view showing the externally threaded hub of the TUBEX closed injection system and collar containing two ears of the first preferred embodiment.

FIG. 4 is an elevational view of collar showing the ears and internal threads of the first preferred embodiment.

FIG. 5 is a partial side view of the second embodiment showing a TUBEX closed injection system in which the hub containing ears is a unitary component.

DETAILED DESCRIPTION OF THE INVENTION

Figure 6:
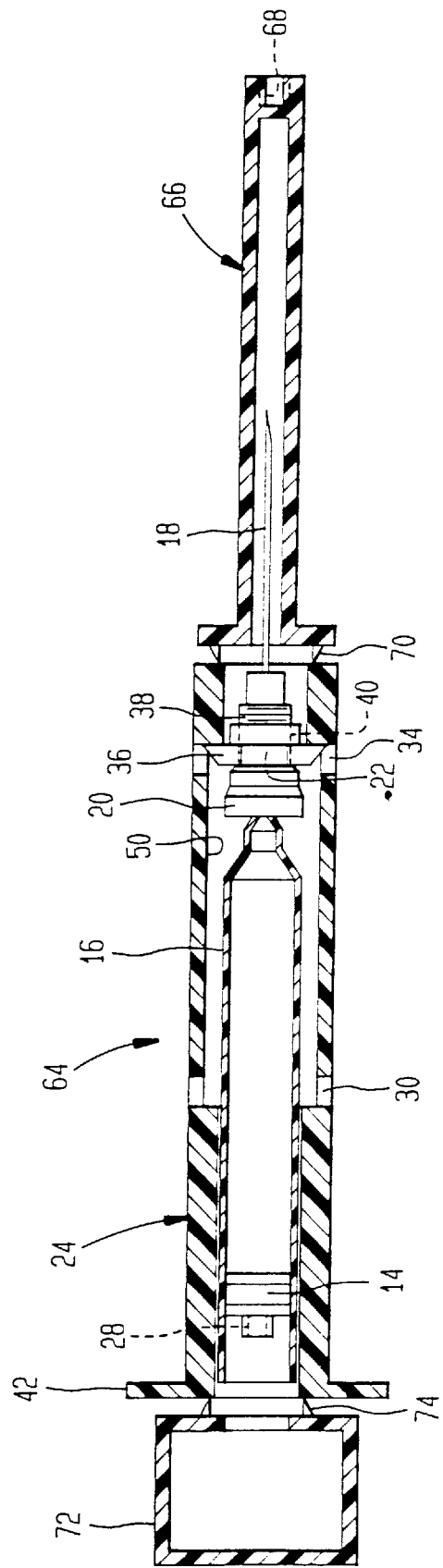
FIG. 6 is a sectional view of the third embodiment showing the TUBEX closed injection system, protective sheath, with the protective sheath in the first position, and the tamper evident sheath cover and needle cover/plunger intact.

In describing the present invention, the term "proximal" or "proximal end" of an element refers to the end of the element furthest from the tip of the needle; and the term "distal" or "distal end" of the element refers to the end of the element closest to the tip of the needle.

With reference to FIGS. 1–4, the first preferred embodiment is shown. The first preferred embodiment (10) comprises a TUBEX closed injection system, plunger (12), a collar (22), and a protective sheath (24). The TUBEX closed injection system is a cartridge syringe having a generally cylindrical cartridge barrel (16), that is preferrably prefilled, made of glass having an internal and external surface in which distal end is constricted, a piston (14), a hub (20) with an axial bore and having external threads (38) mounted to the constricted end of cartridge barrel, and a hollow needle (18), the distal end of the needle having a pointed tip and the proximal end passing through the axial bore of the hub so that when distal pressure is applied by the plunger to the piston, fluid can pass from within the cartridge barrel through the axial bore of the hub and out of the distal end of the needle. The proximal end of the piston has an externally threaded post (28) for engaging the plunger (12) and the distal end of the plunger is internally threaded (26) to receive the externally threaded post of the piston.

Mounted on the external threads of the hub is collar (22) having two ears (36) on opposite sides of the outside of the collar and threads (40) on the inside of the collar. The collar being mounted to the hub via its internal threads. The collar and external threads of the hub are illustrated by FIGS. 3–4.

The hollow cylindrically tubular protective transparent or translucent sheath (24) has two longitudinal channels (50) on opposing sides of the inside of the sheath, a first pocket (34), a second pocket (30), and grasping ears (42). The arrangement of the pockets and longitudinal channels is best shown in FIG. 2. The protective sheath is longer in length than the length of the needle and has an internal diameter greater than the external diameter of the cartridge barrel. Prior to administering an injection, the protective sheath is in the first position so that the ears (36) are disposed inside of the longitudinal channels of the sheath, with the ears being releasably engaged with first pockets (34). In this first position, the tip of the needle extends distally past the distal end of the sheath.

An injection is administered by holding the grasping ears (42) of the protective sheath and applying sufficient distal pressure to the plunger (12) engaged to the piston (14) to force the contents of cartridge barrel out of the needle (18). Following the administration of the injection, it is desirable to prevent accidental needle sticks by shielding the person administering the injection or the patient from the needle. In the first preferred embodiment, this is accomplished by grasping the cartridge barrel (16) in one hand and the sheath with the other hand. Pressure is applied to the sheath from the proximal end, so that the ears (36) are disengaged from the first pockets (34) and sheath is slid toward the tip if the needle with the ears moving within the longitudinal channels of the sheath until the ears engage the second pockets (30) in the second position. In the second position, as illustrated by the view in FIG. 1, the protective sheath extends past the tip of the needle, so that accidental contact with the needle is prevented.

Movement of the sheath is limited to between the first and second positions by virtue of the length of the longitudinal channels and by the shape of the ears. The longitudinal channels run longitudinally within the sheath from the distal side of the first pockets to the proximal side of the second pockets. The ears are shaped so that, when mounted to the hub, the distal side is flat and perpendicular to the longitudinal axis of the sheath and the proximal side of the ears is angularly shaped as illustrated in FIG. 1. The ears extend axially outward slightly further than the inside wall of the sheath in the longitudinal channels so the ears can engage the pockets in the sheath. Either the sheath or the ears must be slightly flexible to allow either expansion of the sheath or compression of the ears while the ears are in the longitudinal channels when the sheath is being moved from the first to the second position. Proximal movement of the ears beyond the first position is prevented, by flat distal side of the ears being in contact with the distal end of the longitudinal channel. The angled shape of the proximal side of the ears allows distal movement of the sheath from the first position following the proximal application of pressure to the sheath when it is in the first position. When the sheath is moved to the second position, the ears and the second pockets are engaged so that the sheath can no longer be moved in either direction. The flat distal side of the ears prevents movement of the sheath proximally and the proximal end of the longitudinal channel prevents movement of the sheath distally beyond the second position. Accidental needle sticks are therefore prevented by locking the sheath in the second position with the sheath extended proximally beyond the tip of the needle.

The second embodiment is a modification of the first preferred embodiment, in which the collar (22) has been replaced by a hub (60) which contains ears (62), as shown in FIG. 5. The ears are shaped the same as the ears described in the first preferred embodiment, and have the same function as in the first preferred embodiment.

The third embodiment, as illustrated in FIG. 6, is a modification of the first embodiment in which the device described in the first embodiment is provided as a preassembled tamper evident syringe assembly (64). In this embodiment, the protective sheath (24) is in the first position, so that the ears (36) are releasably engaged with the first pockets (34), and the tip of the needle extends distally past the end of the sheath. A tamper evident needle cover/plunger (66), having an inside and an outside surface, and a closed distal end, is breakably attached to the distal end of the protective sheath by tamper evident snap ring (70), so that the needle is encased within the needle cover/plunger. The inner surface of the needle cover/plunger can be generally cylindrical or conical, provided that it is longer than the length of the needle, and in its assembled state, as shown in FIG. 6, is snugly engaged around the distal end of the hub (20) by friction fit. The snug friction fit relationship between the inside of the needle cover/plunger and hub prevents contamination of the needle and contents of the cartridge barrel following manufacture. A tamper evident sheath cover (72), having a closed proximal end, is breakably attached to the proximal end of the protective sheath by tamper evident snap ring (74). The snap rings (70) and (74) can be circumferentially solid, typically with one end being tapered to facilitate separation of the protective sheath from the sheath cover and needle cover/plunger, or can be a discontinuous ring, having at least two solid portions, that are preferably tapered. The presence of the sheath cover and needle cover/plunger with intact tamper evident snap rings immediately prior to injection provides an indication that the device was not tampered with following manufacture.

To use the device described in the third embodiment, the user can grasp the protective sheath in one hand and apply a twisting or bending force to the sheath cover with the other hand, separating the snap ring that attaches the sheath cover to the protective sheath from either the sheath cover or the sheath, depending on how the snap ring is designed. As illustrated in FIG. 6, the snap ring would remain attached to the sheath cover. The sheath cover can then be discarded. Similarly, the needle cover/plunger can be separated from the protective sheath, and used as the plunger by attaching the internal threads (68) of the needle cover/plunger to the externally threaded post (28) of the piston (14). The contents of the cartridge barrel can be administered, and protective sheath moved between the first and second positions as described for the first embodiment.

The foregoing is intended to be illustrative of the preferred embodiments of the present invention and is not intended to limit the scope of the present invention as defined by the following claims. Many changes and substitutions that retain the desired function may be made to the disclosed preferred embodiments. For example, the sheath as disclosed is transparent or translucent, however, the sheath may be opaque without preventing the device from functioning as it is intended. The sheath also need not be cylindrically tubular, but can be ovally tubular, or otherwise shaped provided that the ears can be moved within channel between the first and second positions of the sheath. The ears can be shaped differently than described in the preferred embodiment, provided that they allow unidirectional movement of the sheath along the longitudinal axis of the syringe cartridge until a point in which the sheath extends distally past the tip of the needle, where the sheath cannot be retracted backwards. The collar need not be threaded on the hub, but can be mounted on the hub by friction fit if so desired. The protective sheath may have more than two pockets in each longitudinal channel. An intermediate pocket can be placed in the channels to create an intermediate position in which the shield extends distally past the end of the needle only so that the syringe cartridge can be connected to an intravenous line. After use in this manner, the sheath can be moved from the intermediate position to the second position to so that the needle is completely inaccessible. The longitudinal channels can be eliminated if the ears and pockets are shaped in a manner that would allow them to be engaged with out being guided into place by the longitudinal channels. For example, the ears can extend circumferentially around the collar, or the hub so that they can engage the pockets without the need for longitudinal channels. The sheath can be designed with one longitudinal and one the hub having one ear. The pockets can be of any shape provided they can engage the ears. The pockets can be in the form of circumferential grooves in the shield. The internal threads on the plunger can be replaced so that the plunger fits on the external post of the piston by friction fit. Based on this disclosure, other variations of this device that maintain the same function will be apparent to one skilled in the art. Additionally, prefilled syringe cartridges other than the TUBEX closed injection system are known, and can be used with the protective sheath and collar device described in this disclosure.

What is claimed:

1. A device for preventing accidental needle sticks which comprises a syringe cartridge comprising a cartridge barrel with an internal and external surface, the cartridge barrel having a constricted distal end region, a piston movably disposed within the barrel, a hub having external threads and an axial bore mounted to the constricted distal end region of the barrel, and a hollow needle, the proximal end of the hollow needle projecting through the axial bore of the hub and the distal end having a pointed tip;

a protective sheath having an inner diameter greater than the external diameter of the syringe cartridge, the protective sheath having an internal and external surface;

the protective sheath having at least one longitudinal channel on the inside surface of the protective sheath extending from a first position to a second position, the first position being distal to the second position;

the protective sheath having at least two pockets disposed in the longitudinal channel, with the first pocket located at the first position and the second pocket located at the second position; and a collar having an external surface mounted to the external threads of the hub, the collar having at least one ear on the external surface of the collar, the ear being disposed in the longitudinal channel, such that the protective sheath is slideably movable substantially coaxially along the external surface of the cartridge barrel from a first position in which the first pocket and ear are releasably engaged so that the tip of the needle extends distally past both ends of the protective sheath, to a second position in which the ear and second pocket are engaged so that the distal end of the sheath extends past the tip of the needle.

2. The device according to claim 1, wherein the syringe cartridge is prefilled.

3. The device according to claim 2 wherein the collar is internally threaded, and is threadably mounted to the external threads of the hub.

4. The device according to claim 3 wherein the protective sheath contains two longitudinal channels on opposing sides of the internal surface of the sheath and the collar having two ears on opposite sides of the external surface with one ear being disposed in each longitudinal channel.

5. The device according to claim 4 wherein the ears are shaped so that the protective sheath cannot be retracted to a position in which the needle is exposed past the distal end of the protective sheath.

6. The device according to claim 5 wherein the prefilled syringe cartridge is a sterile cartridge needle unit.

7. The device according to claim 2 wherein the prefilled syringe cartridge is a sterile cartridge needle unit.

\* \* \* \* \*